United States Patent
Diehl et al.

(10) Patent No.: US 9,222,912 B2
(45) Date of Patent: Dec. 29, 2015

(54) METHOD FOR CORRECTING THE PUMP CURRENT OF A SENSOR ELEMENT

(75) Inventors: Lothar Diehl, Gerlingen (DE); Goetz Reinhardt, Boeblingen (DE); Thomas Seiler, Stuttgart (DE); Hartwig Lehle, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 536 days.

(21) Appl. No.: 13/808,615

(22) PCT Filed: Jun. 27, 2011

(86) PCT No.: PCT/EP2011/060680
§ 371 (c)(1),
(2), (4) Date: Mar. 21, 2013

(87) PCT Pub. No.: WO2012/004143
PCT Pub. Date: Jan. 12, 2012

(65) Prior Publication Data
US 2013/0167511 A1 Jul. 4, 2013

(30) Foreign Application Priority Data
Jul. 7, 2010 (DE) .......................... 10 2010 031 060

(51) Int. Cl.
| | | |
|---|---|---|
| G01N 27/41 | (2006.01) | |
| F02D 41/14 | (2006.01) | |
| F02D 41/28 | (2006.01) | |
| G01N 27/406 | (2006.01) | |
| G01N 27/417 | (2006.01) | |
| G01N 27/419 | (2006.01) | |

(52) U.S. Cl.
CPC ............ *G01N 27/41* (2013.01); *F02D 41/1493* (2013.01); *F02D 41/28* (2013.01); *G01N 27/4065* (2013.01); *G01N 27/419* (2013.01); *G01N 27/4175* (2013.01); *F01N 2560/025* (2013.01); *F02D 2041/1432* (2013.01); *F02D 2041/288* (2013.01)

(58) Field of Classification Search
CPC ... F01N 2560/25; G01N 27/409; G01N 27/41
See application file for complete search history.

(56) References Cited

U.S. PATENT DOCUMENTS

| 8,245,566 B2 | 8/2012 | Wehmeier et al. |
| 2009/0038941 A1 | 2/2009 | Stahl et al. |
| 2010/0003173 A1 | 1/2010 | Muller et al. |

FOREIGN PATENT DOCUMENTS

| DE | 10 2004 023 004 | 12/2005 |
| DE | 10 2004 042 027 | 3/2006 |

(Continued)

OTHER PUBLICATIONS

EPO computer-generated English language translation of DE 102007045984 A1, patent published Apr. 2, 2009.*

(Continued)

*Primary Examiner* — Alex Noguerola
(74) *Attorney, Agent, or Firm* — Kenyon & Kenyon LLP

(57) ABSTRACT

A method for operating a sensor element, in particular a lambda sensor, for determining the concentration of a gas component of a gas mixture, in which the gas component is removed from a measuring gas chamber by applying a pump voltage and the concentration of the gas component in the gas mixture is inferred therefrom. Oscillations of the pump current caused by dynamic pressure variations are taken into consideration for a correction of the sensor signal in that a frequency analysis of the pump current is carried out.

10 Claims, 3 Drawing Sheets

(56) References Cited

FOREIGN PATENT DOCUMENTS

| | | |
|---|---|---|
| DE | 10 2007 045 984 | 4/2009 |
| DE | 10 2008 042 549 | 4/2010 |
| EP | 1 006 353 | 6/2000 |
| JP | 2010-38794 | 2/2010 |

OTHER PUBLICATIONS

EPO computer-generated English language translation of DE 102008042549 A1, patent published Apr. 8, 2010.*

International Search Report, PCT International Application No. PCT/EP2011/060680, dated Sep. 8, 2011.

* cited by examiner

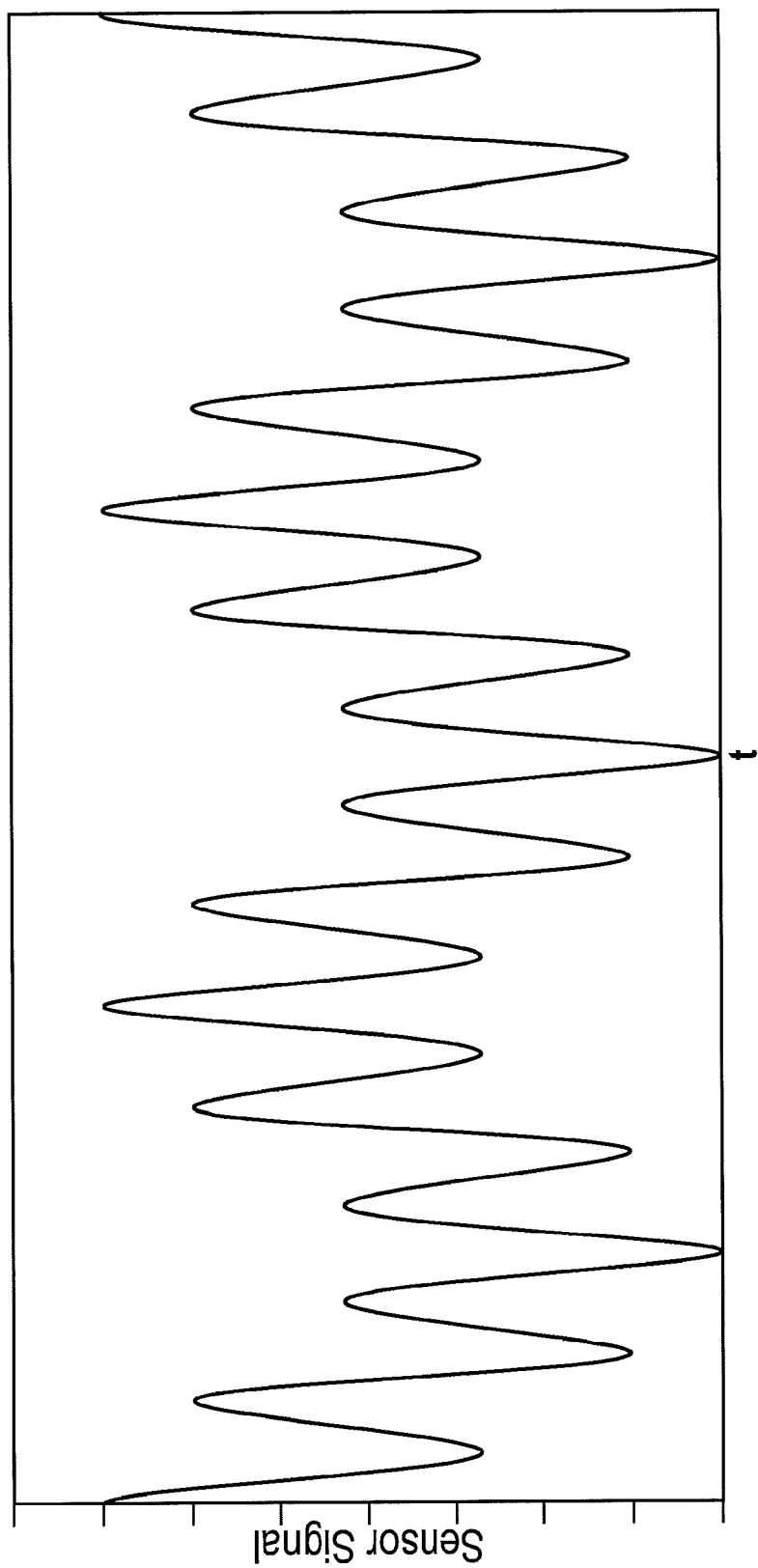

METHOD FOR CORRECTING THE PUMP CURRENT OF A SENSOR ELEMENT

FIELD

The present invention relates to a method for operating a sensor element, in particular a broadband lambda sensor.

BACKGROUND INFORMATION

Various sensor elements for determining the concentration of a gas component in gas mixtures are available. Thus, for example, so-called lambda sensors are used to determine the excess-air coefficient, which describes the ratio of air to fuel. This ratio is of decisive significance for the combustion of the fuel in an internal combustion engine and for the exhaust gas aftertreatment.

Conventional discrete-level sensors and broadband sensors may measure the residual oxygen content in the exhaust gas. In a discrete-level sensor, the potential of an exhaust-side electrode is measured in relation to an oxygen-flushed reference electrode. A discrete-level sensor may recognize the transition from a rich mixture to a lean mixture and vice versa. A broadband lambda sensor may measure the residual oxygen content in the exhaust gas over a substantially wider range, i.e., both in the rich range and also in the lean range. It generally includes a combination of a typical concentration sensor (Nernst sensor) acting as a galvanic cell and a limiting current or "pump" cell. A voltage is externally applied to the pump cell. If the voltage is sufficiently high, a limiting current results, which is proportional to the difference of the oxygen concentration on both sides of the cell. Oxygen atoms are transported with the current as a function of the polarity. Precisely enough oxygen from the exhaust gas is always supplied to the concentration sensor from the pump cell by an electronic control circuit so that the state $\lambda=1$ prevails. The particular pump current, which is proportional to the oxygen content or rich gas content in the exhaust gas, forms the output signal of the broadband lambda sensor. The measurement of the concentration in the measuring gas chamber is performed on the basis of the determination of the Nernst voltage between a Nernst electrode in the measuring gas chamber and an oxygen-flushed reference electrode in a reference chamber. In order to reach the operating temperature required for the oxygen ion transport, a broadband lambda sensor is equipped with an integrated heating device.

The measuring signal of the lambda sensor is a function of both the excess-air coefficient $\lambda$, i.e., the ratio of air to fuel in the mixture, and also the prevailing absolute pressure. The absolute pressure of the exhaust gas varies by several hundred millibars with the frequency of the cylinder ignition of the internal combustion engine. With each pressure pulse, the quantity of lean or rich gas components transported into the measuring gas chamber of the lambda sensor is briefly strongly increased and subsequently strongly decreased again. Since the controller of the pump current reacts very rapidly, it can pump out rapidly in the phase of transporting in the additional gas components, which represent a deviation from the setpoint concentration in the cavity of $\lambda=1$. Therefore, fewer gas components are transported out in the subsequent low-pressure phase than were transported in during the high-pressure phase. The occurring oscillations of the pump current may be smoothed by a suitable electronic filter. Overall, however, a shift of the mean pump current occurs, which is accompanied by a loss of characteristic curve precision.

An approach for minimizing the inaccuracy accompanying this uses the densest possible embodiment of the diffusion barriers, which separate the exhaust gas from the measuring gas chamber. However, the static pressure dependence of the lambda sensor is increased in this way. Another measure for reducing the effects of the dynamic pressure dependence is to shrink the volume of the measuring gas chamber in comparison to the volume of the diffusion barrier, as described in German Patent Application No. DE 10 2004 023 004 A1, for example. The dependence of the measuring signal on the dynamic pressure variations may also be decreased in this way. However, shrinking the measuring gas chamber may also result in other disadvantages. Due to the high diffusion resistance of the cavity, the oxygen is only pumped out at the front edge of the electrode in this case and thus the electrode is locally overloaded. This is true in particular for poisoning by gaseous electrode poisons transported thereto.

The present invention relates to an example method for operating a sensor element, in particular a broadband lambda sensor, which allows reliable compensation of the dynamic pressure dependence of the pump current and therefore increases the measuring precision of the sensor element. The example method is also to be able to be used in existing sensor elements, without further modifications having to be made on the sensor element itself.

SUMMARY

An example method according to the present invention is provided for operating a sensor element, in particular a lambda sensor, which is suitable for determining the concentration of a gas component in a gas mixture. The gas component is removed from the measuring gas chamber by applying a pump voltage and the concentration of the gas component in the gas mixture is inferred therefrom. Such sensor elements may be, in particular, broadband lambda sensors, which function according to the so-called two-cell principle or according to the so-called one-cell principle. According to the two-cell principle, the concentration of the gas component in the measuring gas chamber is regulated to a predefinable value and the concentration of the gas component in the gas mixture is inferred from the pump current measured at this time. In a one-cell sensor, the concentration of the gas component is measurable on the basis of a limiting current. The method according to the present invention is characterized in that oscillations of the pump current which are caused by dynamic pressure variations are taken into consideration for a correction of the pump current. Dynamic pressure variations which result with the frequency of the cylinder ignition of the internal combustion engine, for example, finally influence the pump current and therefore the measuring signal of the sensor element. The core of the present invention is to identify these oscillations generated by dynamic pressure variations or the frequency components thereof and to correct the sensor signal accordingly. The specific mean value shift of the pump current which is caused by the pressure oscillations may thus be compensated for, whereby the measuring precision of the sensor element is significantly improved.

The oscillations of the pump current are preferably analyzed to identify the frequency components which are caused by the dynamic pressure variations. The pump current is corrected by the frequency components which are caused by the dynamic pressure variations. These frequency components are also referred to hereafter as the frequency components of the pressure variations. The identification of the frequency components of the pressure variations and their compensation may be carried out particularly advantageously as a function of software of the operating electronics. No further adaptations of the sensor element itself are necessary.

Rather, the example method according to the present invention may be used by adapting or supplementing the analysis software of a sensor element, so that the method according to the present invention may also be used in existing sensor elements.

The analysis of the oscillations is particularly advantageously performed by a frequency analysis. The oscillations which are caused by variations in the ratio of air to fuel or by lambda variations have a lower frequency than the oscillations which are caused by dynamic pressure variations. Due to these differences, the lambda oscillations may be separated from the pressure oscillations, so that the frequency components of the pressure variations may be identified and taken into consideration for a correction according to the present invention. In a particularly preferred specific embodiment, the analysis of the frequencies is performed by a Fourier frequency analysis, i.e., a decomposition of the oscillations into their various sine and cosine functions, in order to thus differentiate the frequency components which originate from the lambda oscillations, on the one hand, and from the dynamic pressure variation oscillations, on the other hand.

For the correction of the sensor signal according to the present invention, the frequency components which are caused by the dynamic pressure variations may be subtracted from the oscillations of the pump current, so that finally only the lambda oscillations have an effect in the analysis of the measuring signal of the sensor element.

In another preferred embodiment of the method according to the present invention, the correction of the sensor signal may be performed with the aid of a characteristics map. The shift described at the outset of the mean pump current as a result of the oscillations or oscillation components of the pump current caused by dynamic pressure changes is characterized by a so-called specific mean value shift. This specific mean value shift is a function of both the sensor type and also the frequency of the pressure variations and the prevailing mean pressure. The shape and amplitude of the pressure pulses have no influence on this variable. The specific mean value shift may therefore be assigned to an instantaneous, operating-point-dependent combination of amplitude, frequency, and form factor of a sensor-typical shift of the mean pump current. This relationship may be stored, for example, in the form of a characteristics map in an analysis and/or control unit. The shift of the mean pump current is calculated from the instantaneous, operating-point-dependent combination of pressure pulse amplitude and shape and from the specific mean value shift taken from the characteristics map. On the basis of this characteristics map, the measured pump current or the sensor signal and the error in the lambda measurement connected thereto may be shifted or corrected to compensate for the specific mean value shift as a result of the dynamic pressure dependence of the pump current. It is also possible to determine the amplitude and the form factor of the pressure pulses as a function of the operating point, for example, with the aid of a characteristics map or, in a particularly preferred way, with the aid of a dynamic pressure model. Such pressure models are used, for example, in the context of the compensation of the static pressure dependence of the sensor signal in a similar way. The frequency of the pressure pulses may be derived here from the engine speed, for example. In summary, the frequency components of the oscillations caused by dynamic pressure variations may thus be characterized by at least one variable, which is assigned to a sensor-element-typical mean value shift of the pump current, for example, in the form of a characteristics map. The correction of the pump current may be performed on the basis of this assignment. In other specific embodiments, the relationship between the frequency components which are caused by dynamic pressure variations and operating variables or operating conditions which are measurable or derivable are summarized with the aid of a dynamic pressure model, so that the oscillations of the pump current caused by dynamic pressure variations or their pressure-variation-related frequency components may be ascertained on the basis of one or more operating variables, to be able to be taken into consideration according to the present invention for the correction of the sensor signal.

Only those frequency components caused by dynamic pressure variations whose frequencies are above a predefinable threshold are advantageously taken into consideration for the correction of the sensor signal. Since the pressure pulses are small in absolute value at low frequencies, it may be sufficient in the meaning of a simplified embodiment for the compensation method according to the present invention to analyze only the high frequencies. In particular at the high frequencies, the contribution to the mean value shift of the measuring signal is particularly relevant. This specific embodiment of the method according to the present invention is less complex than the consideration of all frequencies and may nonetheless significantly improve the measuring precision of the sensor element.

In a particularly preferred specific embodiment of the method according to the present invention, exclusively low frequencies are differentiated from high frequencies during the analysis of the oscillations of the pump current. Low frequencies are preferably those less than 25 Hz, high frequencies are preferably those greater than 25 Hz. This simplified frequency analysis, for example, in the form of a (fast) Fourier transform, may be carried out with little effort and nonetheless achieves very advantageous results. In this case, for example, the signal of the sensor may be conducted through a high-pass filter and rectified. The averaged amplitude is used as a parameter for the sensor signal correction. In addition, the shift of the mean pump current which occurs as a result of the pressure pulses is to be taken into consideration in this specific embodiment.

The shape, amplitude, and frequency of the pressure pulses change relatively slowly in comparison to their period duration. The rich-lean oscillations of the mixture regulation and changes in the excess-air coefficient due to load changes also typically occur at frequencies of approximately only 10 Hz. These relatively slow changes therefore allow sufficiently rapid compensation according to the present invention in adaptation to a new operating point.

According to the present invention, further interference signals may also be taken into consideration in the correction of the pump current. In particular, the interference signal of the pump current due to the passage of the exhaust gas concentration at $\lambda=1$ may additionally be compensated for. During the passage of the exhaust gas concentration through $\lambda=1$, for example, the interference signal may be ascertained from the slope of the pump current change on the basis of a characteristics map of the interference signal stored in the software and subtracted from the measured pump current. The interference signal of the pump current due to cross-talk of the heater cycling of the sensor element may also be taken into consideration according to the present invention. This interference signal may be ascertained, for example, from the heat output, the activation signals, in particular the duty cycle of the heater, and the heating resistance of the heater, and optionally the engine operating point, the exhaust gas temperature, etc., on the basis of a characteristics map stored in the software and subtracted from the measured pump current. A corresponding characteristics map may be recalibrated in suitable operating phases, in that the unfiltered and uncompensated interference signal of the pump current is measured when the heater is coupled in and stored.

Furthermore, the present invention includes a computer program which executes all steps of the example method according to the present invention when it runs on a computer unit or a control unit. Finally, the present invention includes a computer program product having program code which is stored on a machine-readable carrier, for carrying out the example method according to the present invention when the program is executed on a computer or a control unit. With the aid of the computer program or the computer program product, the example method according to the present invention may also readily be used in existing sensor elements and utilized therein to compensate for oscillations or oscillation components of the pump current which are caused by dynamic pressure variations. Dynamic pressure variations which arise as a result of a varying absolute pressure of the measured gas, in particular as a result of the frequency of the cylinder ignition, corrupt the measuring signal of a sensor element, in particular a broadband lambda sensor, whereby a shift of the mean pump current (specific mean value shift) takes place. The specific mean value shift may be compensated for according to the present invention in that the pump current is corrected by the frequency components which are caused by the pressure variations.

BRIEF DESCRIPTION OF THE DRAWINGS

Further features and advantages of the present invention result from the following description of exemplary embodiments in the context of the figures. The various features may each be implemented alone or in combination with one another here.

DETAILED DESCRIPTION OF EXAMPLE EMBODIMENTS

Figure 1:
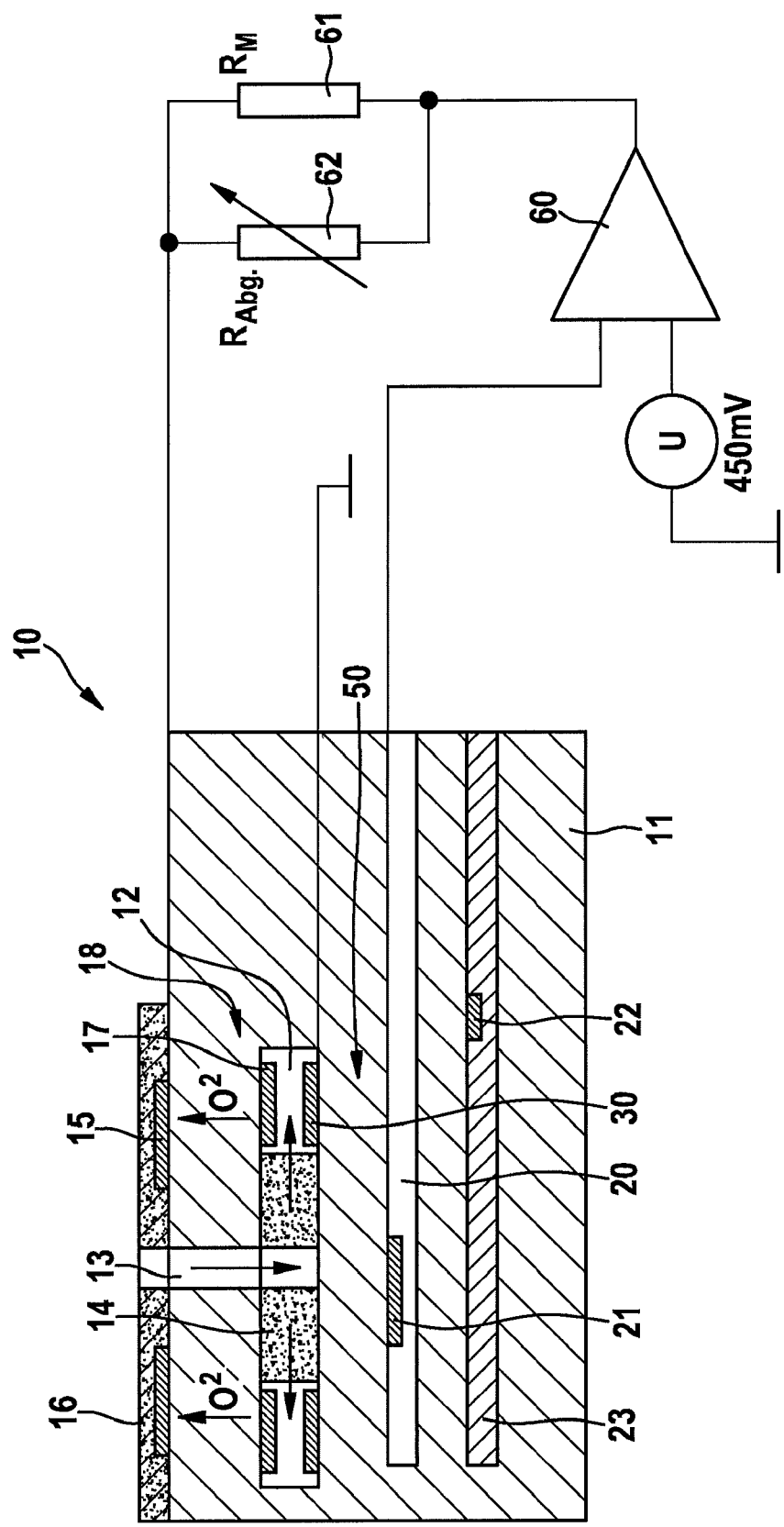
FIG. 1 shows a conventional broadband lambda sensor.

FIG. 1 shows a conventional broadband lambda sensor which is provided for determining the oxygen concentration in a gas mixture, in particular in the exhaust gas of an internal combustion engine. The sensor element includes a planar sensor body 10, which is formed from a solid electrolyte 11 and in which a ring-shaped cavity 12, for example, is designed as the measuring gas chamber. Cavity 12 is connected via a central opening 13 to the exhaust gas. A porous diffusion barrier 14 is situated between central opening 13 and cavity 12. An outer pump electrode 15, which is covered by a porous protective layer 16, is situated on the side of opening 13. An inner pump electrode 17 is situated on the side of measuring gas chamber 12 facing away from outer pump electrode 15. Outer pump electrode 15 and inner pump electrode 17 delimit a pump cell 18, which is provided for the transport of oxygen ions.

A reference electrode 21 is provided inside a reference gas volume 20. A further electrode, Nernst electrode 30, is situated inside measuring gas chamber 12, the Nernst electrode being at a zero potential like inner pump electrode 17. Nernst electrode 30 and reference electrode 21 together form a Nernst or concentration cell 50.

Furthermore, a heater 22 is situated in a heater insulation layer 23 below measuring gas chamber 12 and reference gas volume 20. Heater 22 may be designed as meandering, for example. Heater 22 ensures an adequate operating temperature of sensor element 10.

A measuring and analysis circuit of sensor element 10 includes a differential amplifier 60, to one input of which a reference voltage is applied, in particular 450 mV. The other input is connected to reference electrode 21. Furthermore, a current divider, including a measuring resistor $R_M$ 61 and a compensation resistor $R_{Abg}$ 62, is provided, which conducts the output of differential amplifier 60 to outer pump electrode 15.

A pump voltage is applied to electrodes 15 and 17 of pump cell 18, with the aid of which a constant oxygen partial pressure is set in measuring gas chamber 12 by pumping oxygen in or out. The pump voltage is regulated in such a way that a constant voltage value of, for example, 450 mV results at electrodes 30 and 21 of concentration cell 50. This voltage corresponds to a value of $\lambda=1$. According to this so-called double-cell principle, the excess-air coefficient in measuring gas chamber 12 is regulated by the pump current to a predefinable value, which is preferably kept constant at $\lambda=1$. This excess-air coefficient in the measuring gas chamber is predefined by the predefinable comparison voltage for the Nernst cell, in this case 450 mV.

The measurable signal is a function, on the one hand, of the air concentration in the exhaust gas mixture, i.e., of the excess-air coefficient of the gas mixture. On the other hand, the measuring signal is also influenced by the absolute pressure. It is problematic here that the absolute pressure of the exhaust gas is subject to variations. For example, the absolute pressure oscillates with the frequency of the cylinder ignition by several hundred millibars. With each pressure pulse, a short-term strong increase of the lean or rich gas components of the exhaust gas transported into measuring gas chamber 12 occurs. The measuring and analysis circuit of sensor element 10 may react very rapidly thereto, so that the additional gas components penetrating in the phase of transporting in during the pressure pulse, which cause a deviation from $\lambda=1$ in measuring gas chamber 12, are transported out very rapidly via pump cell 18. Overall, however, a shift of the measuring signal occurs, since fewer gas components are transported out in the subsequent low-pressure phase than were transported in during the high-pressure phase. Even in the case of smoothing of these pump current oscillations by suitable electronic filtering, a shift of the mean pump current occurs, which impairs the measuring precision.

This problem does not occur in only the double-cell principle of a broadband lambda sensor shown in detail here. Lambda sensors according to the so-called one-cell principle, in which excess-air coefficient $\lambda$ is measurable on the basis of a limiting current, also display a comparable mean value shift of the limiting current as a result of dynamic pressure variations. Therefore, an example method according to the present invention may also be used with particular advantage during the operation of a lambda sensor according to the one-cell principle.

According to an example embodiment of the present invention, the oscillations of the pump current caused by the dynamic pressure variations, i.e., the frequency components which are caused by the dynamic pressure variations, are compensated for during a correction of the sensor signal, so that the shift of the mean pump current caused by the pressure pulses is corrected. The measuring precision of a sensor element operated in this way may thus be substantially improved. System tolerances may also be reduced by this measure. The oscillations are preferably analyzed to identify the frequency components of the oscillations of the pump current caused by the dynamic pressure variations. For example, a Fourier frequency analysis may be carried out for this purpose, in the case of which the periodic signals of the pump current are decomposed into their individual frequency components. These frequency components may be subtracted from the measured pump current, for example.

In another particularly preferred specific embodiment, the instantaneous, operating-point-dependent combination of amplitude, frequency, and form factor of the pressure variations of a sensor-typical shift of the mean pump current is assigned in a characteristics map to the specific mean value shift, so that on the basis of this characteristics map, solely by measuring the instantaneous pump current and considering the particular operating point, the specific mean value shift may be ascertained and the lambda measurement may be corrected accordingly. In other specific embodiments, a dynamic pressure model may be used for this purpose. The amplitude and the form factor of the pressure pulses are determined here as a function of the operating point with the aid of the dynamic pressure model. The frequency of the pressure pulses results from the engine speed.

In a preferred way, the example method according to the present invention is used in engines whose cylinder equalization is already ensured from the engine smoothness or other methods. In this case, the pump current signal generally contains no components having high frequencies which would have been generated by lambda differences. Rather, only variations due to the pressure pulses are to be expected in the high-frequency range. In general, the variations below a specific frequency threshold, for example, below 25 Hz, are caused by actual lambda variations. Above this threshold, the oscillations are in principle caused by pressure pulses. To a certain extent, oscillations which are to be attributed to lambda variations also occur above 25 Hz. These lambda variations are caused by cylinder misalignments. Since they occur in principle at half of the frequency of the pressure pulses, they may be differentiated well therefrom in the frequency spectrum. When cylinder equalization is ensured, the variations above the specific threshold, e.g., 25 Hz, are generally caused only by pressure pulses. In the event of sudden changes in the exhaust gas composition, the frequency spectrum of the lambda variations becomes wider, so that the tails of this spectrum may also provide a contribution above this threshold. These tails are flatter than the contributions of the pressure pulses, however, and may thus be differentiated therefrom.

In the case of trimmed cylinders, it is preferable to decompose the oscillations of the pump current by a frequency analysis into the frequency components, if the lambda variations excessively overlap with the pressure pulses. Since the lambda variations have at most half of the frequency as the pressure pulses due to the cylinder trimming, it is readily possible to differentiate the frequency components from one another in a Fourier spectrum, for example.

Preferably, the Fourier amplitude, which is to be assigned in particular to twice the engine speed, is analyzed, since it may be reliably assigned to the pressure variations.

Figure 2B:
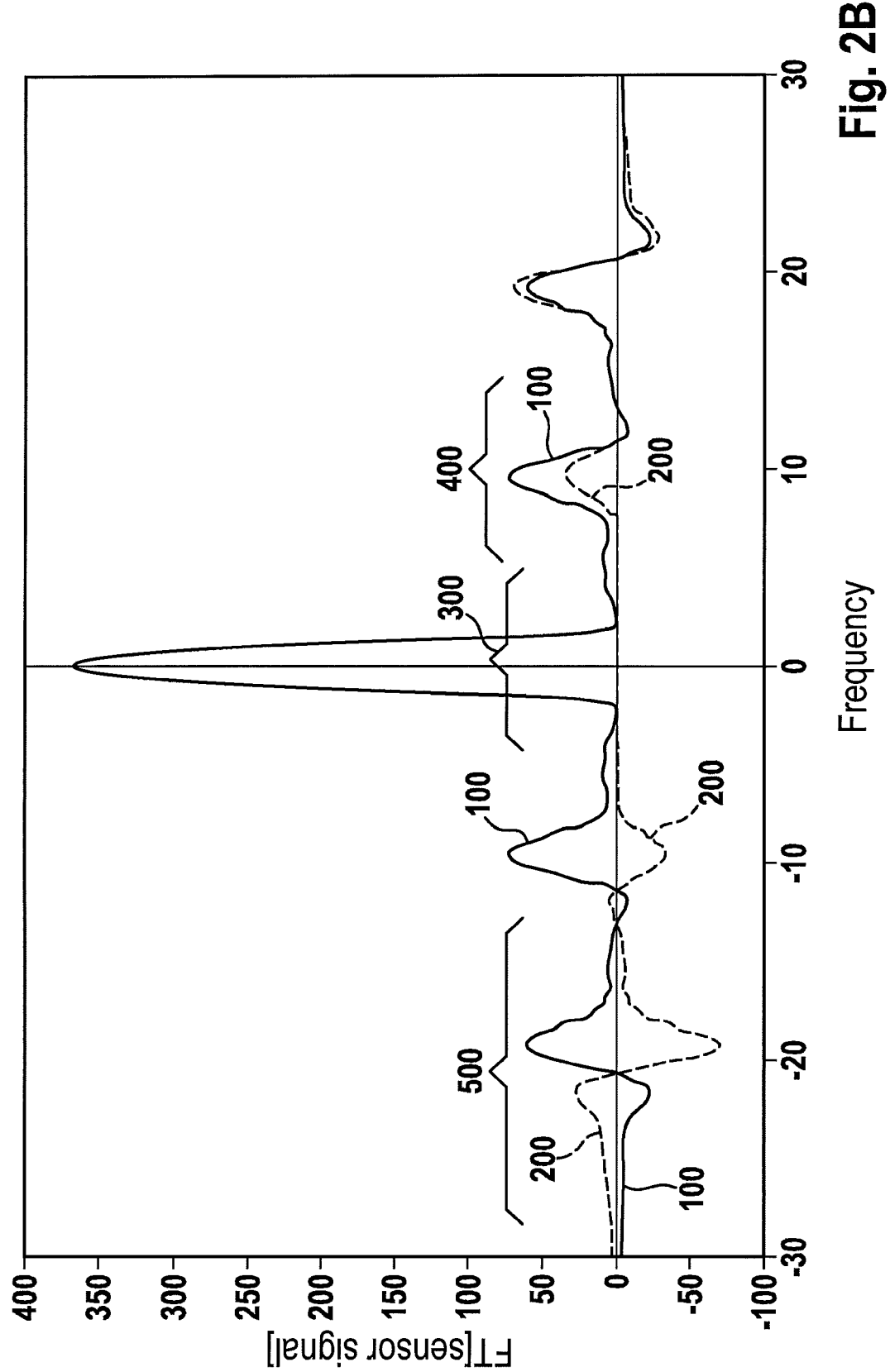
FIG. 2 shows a schematic view of the sensor signal with superimposed pressure pulses and gas exchanges (FIG. 2A) and a Fourier spectrum of the sensor signal (FIG. 2B).

FIG. 2A shows a schematic view of the time curve of the sensor signal with superimposed pressure pulses and gas exchanges (lambda change). FIG. 2B shows the associated Fourier decomposition (FT [sensor signal]). The curve of the signal in FIG. 2B identified by reference numeral 100 shows the real part (FT [lp]) of the sensor signal. The curve identified by reference numeral 200 shows the imaginary part (FT [lp]) of the sensor signal. The area identified by reference numeral 300 indicates static pump current lp. The signals in the Fourier spectrum above static lp 300 are to be assigned to a gas exchange or lambda change, identified here by reference numeral 400. Signals in the Fourier spectrum above these frequencies are to be assigned to pressure pulses, identified here by reference numeral 500. The influence of the pressure pulses may therefore be separated from the actual lambda signal. However, the shift of the mean pump current, which causes an additional contribution at the frequency 0 Hz, is also to be corrected for this purpose.

What is claimed is:

1. A method for operating a lambda sensor for determining a concentration of a gas component of a gas mixture, comprising:
    removing the gas component from a measuring gas chamber by applying a pump voltage, the concentration of the gas component in the gas mixture being inferred therefrom; and
    correcting a sensor signal of the sensor taking into consideration oscillations of the pump current caused by dynamic pressure variations.

2. The method as recited in claim 1, wherein the oscillations of the pump current are analyzed to identify those frequency components caused by dynamic pressure variations and the sensor signal is corrected by the frequency components of the dynamic pressure variations.

3. The method as recited in claim 2, wherein the analysis of the oscillations is carried out by a Fourier frequency analysis.

4. The method as recited in claim 2, wherein the frequency components caused by dynamic pressure variations are subtracted from the oscillations of the pump current.

5. The method as recited in claim 2, wherein at least one variable, which characterizes the frequency components caused by dynamic pressure variations, has assigned to it a sensor-element-typical mean value shift of the pump current, and the correction of the sensor signal is performed on the basis of the assignment, the assignment being stored in a characteristics map.

6. The method as recited in claim 2, wherein only those frequency components caused by dynamic pressure variations whose frequencies are above a predefinable threshold are taken into consideration for the correction of the pump current.

7. The method as recited in claim 2, wherein frequencies less than 25 Hz, and frequencies greater than 25 Hz, are differentiated from one another in the analysis of the oscillations.

8. The method as recited in claim 2, wherein the sensor signal is conducted through a high-pass filter and a rectified and averaged amplitude of the signal is used for a correction of the sensor signal.

9. A computer readable medium storing a computer program for operating a lambda sensor for determining a concentration of a gas component of a gas mixture, the computer program, when executed by a computer, causing the computer to perform the steps of:
    removing the gas component from a measuring gas chamber by applying a pump voltage, the concentration of the gas component in the gas mixture being inferred therefrom; and
    correcting a sensor signal of the sensor taking into consideration oscillations of the pump current caused by dynamic pressure variations.

10. A machine-readable carrier storing a computer program for operating a lambda sensor for determining a concentration of a gas component of a gas mixture, the computer program, when executed by a computer, causing the computer to perform the steps of:

removing the gas component from a measuring gas chamber by applying a pump voltage, the concentration of the gas component in the gas mixture being inferred therefrom; and correcting a sensor signal of the sensor taking into consideration oscillations of the pump current caused by dynamic pressure variations.

\* \* \* \* \*